US009731111B2

(12) United States Patent
DeRohan et al.

(10) Patent No.: US 9,731,111 B2
(45) Date of Patent: Aug. 15, 2017

(54) SYSTEMS AND METHODS FOR MAKING AND USING IMPROVED CONNECTORS FOR ELECTRICAL STIMULATION SYSTEMS

(71) Applicant: BOSTON SCIENTIFIC NEUROMODULATION CORPORATION, Valencia, CA (US)

(72) Inventors: Robert DeRohan, Nipomo, CA (US); Aditya Vasudeo Pandit, Costa Mesa, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 500 days.

(21) Appl. No.: 14/171,335

(22) Filed: Feb. 3, 2014

(65) Prior Publication Data

US 2014/0148885 A1 May 29, 2014

Related U.S. Application Data

(62) Division of application No. 13/430,270, filed on Mar. 26, 2012, now Pat. No. 8,682,439.
(Continued)

(51) Int. Cl.
*A61N 1/05* (2006.01)
*H01R 13/18* (2006.01)
(Continued)

(52) U.S. Cl.
CPC ............ *A61N 1/05* (2013.01); *A61N 1/0551* (2013.01); *H01R 13/18* (2013.01);
(Continued)

(58) Field of Classification Search
CPC ...... A61N 1/05; A61N 1/0551; A61N 1/3752; A61N 1/0553; H01R 13/18
(Continued)

(56) References Cited

U.S. PATENT DOCUMENTS 6,181,969 B1   1/2001  Gord
6,430,442 B1   8/2002  Peters et al.
(Continued)

OTHER PUBLICATIONS

U.S. Appl. No. 12/177,823, filed Jul. 22, 2008.
U.S. Appl. No. 13/430,270 Official Communication mailed Mar. 28, 2013.

*Primary Examiner* — Michael Kahelin
*Assistant Examiner* — Minh Duc Pham
(74) *Attorney, Agent, or Firm* — Lowe Graham Jones PLLC; Bruce E. Black

(57) ABSTRACT

A connector for an implantable medical device includes a lumen extending from a port defined along a length of a connector housing. Axially-spaced-apart connector couplers are disposed along the lumen and are configured to couple to a proximal end of an inserted lead or lead extension. Each of the connector couplers includes a plurality of circumferentially-spaced-apart coupling members and at least one elastic member. The plurality of circumferentially-spaced-apart coupling members each have inner surfaces and outer surfaces. The inner surfaces of the coupling members are configured and arranged to couple to the proximal end of the lead or lead extension when the proximal end of the lead or lead extension is inserted into the lumen. The at least one elastic member couples the coupling members to one another such that a distance between the coupling members is expandable.

20 Claims, 11 Drawing Sheets

Related U.S. Application Data

(60) Provisional application No. 61/473,574, filed on Apr. 8, 2011.

(51) Int. Cl.
*A61B 18/00* (2006.01)
*A61N 1/375* (2006.01)
*H01R 24/58* (2011.01)
*H01R 107/00* (2006.01)

(52) U.S. Cl.
CPC ............... *A61B 2018/0022* (2013.01); *A61B 2018/00214* (2013.01); *A61N 1/3752* (2013.01); *H01R 24/58* (2013.01); *H01R 2107/00* (2013.01); *H01R 2201/12* (2013.01)

(58) Field of Classification Search
USPC ........................................................ 607/59
See application file for complete search history.

(56) References Cited

U.S. PATENT DOCUMENTS

| | | | |
|---|---|---|---|
| 6,498,952 B2 * | 12/2002 | Imani | A61N 1/3752 607/37 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,110,827 B2 | 9/2006 | Sage et al. | |
| 7,164,951 B2 * | 1/2007 | Ries | A61N 1/3752 607/37 |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 8,473,061 B2 | 6/2013 | Moffitt et al. | |
| 8,600,518 B2 | 12/2013 | Meadows et al. | |
| 2003/0163171 A1 * | 8/2003 | Kast | A61N 1/3752 607/36 |
| 2004/0059392 A1 | 3/2004 | Parramon et al. | |
| 2005/0137665 A1 * | 6/2005 | Cole | A61N 1/0553 607/116 |
| 2005/0165465 A1 | 7/2005 | Pianca et al. | |
| 2007/0150036 A1 | 6/2007 | Anderson | |
| 2007/0219595 A1 | 9/2007 | He | |
| 2008/0071320 A1 | 3/2008 | Brase | |
| 2009/0187222 A1 | 7/2009 | Barker | |
| 2009/0287191 A1 | 11/2009 | Ferren et al. | |
| 2010/0076535 A1 | 3/2010 | Pianca et al. | |
| 2010/0268298 A1 | 10/2010 | Moffitt et al. | |
| 2012/0203302 A1 * | 8/2012 | Moffitt | A61N 1/0529 607/45 |

\* cited by examiner

SYSTEMS AND METHODS FOR MAKING AND USING IMPROVED CONNECTORS FOR ELECTRICAL STIMULATION SYSTEMS

CROSS-REFERENCE TO RELATED APPLICATIONS

This application is a divisional of U.S. patent application Ser. No. 13/430,270 filed Mar. 26, 2012, now allowed, which claims the benefit under 35 U.S.C. §119(e) of U.S. Provisional Patent Application Ser. No. 61/473,574 filed on Apr. 8, 2011, which is incorporated herein by reference.

FIELD

The present invention is directed to the area of implantable electrical stimulation systems and methods of making and using the systems. The present invention is also directed to implantable electrical stimulation systems having improved connector assembly designs, as well as methods of making and using the connector assemblies and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for an implantable medical device includes an elongated connector housing having a first end, a second end, and a length. The connector housing defines a port at the second end of the connector housing. The port is configured and arranged for receiving a proximal end of a lead or lead extension. A lumen extends from the port along at least a portion of the length of the connector housing. A plurality of axially-spaced-apart connector couplers are disposed along the lumen such that the connector couplers are each exposed within the lumen. The connector couplers are configured and arranged for coupling to a proximal end of a lead or lead extension when the proximal end of the lead or lead extension is inserted into the lumen. Each of the connector couplers includes a plurality of circumferentially-spaced-apart coupling members and at least one elastic member. The plurality of circumferentially-spaced-apart coupling members each have inner surfaces and outer surfaces. The inner surfaces of the coupling members are configured and arranged to couple to the proximal end of the lead or lead extension when the proximal end of the lead or lead extension is inserted into the lumen. The at least one elastic member couples the coupling members to one another such that a distance between the coupling members is expandable.

In another embodiment, a connector for an implantable medical device includes an elongated connector housing having a first end, a second end, and a length. The connector housing defines a port at the second end of the connector housing. The port is configured and arranged for receiving a proximal end of a lead or lead extension. A lumen extends from the port along at least a portion of the length of the connector housing. A plurality of axially-spaced-apart, substantially-cylindrical connector contact housings are disposed along the lumen. The plurality of connector contact housings each have an inner diameter and an outer diameter. For each connector contact housing the inner diameter forms a portion of a wall of the lumen. A plurality of spherically-shaped connector contacts are disposed on or in each of the connector contact housings such that at least a portion of each of the connector contacts extends into the lumen. For each connector contact housing each of the plurality of connector contacts are configured and arranged for coupling to a different single terminal disposed on a proximal end of a lead or lead extension when the proximal end of the lead or lead extension is inserted into the lumen.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
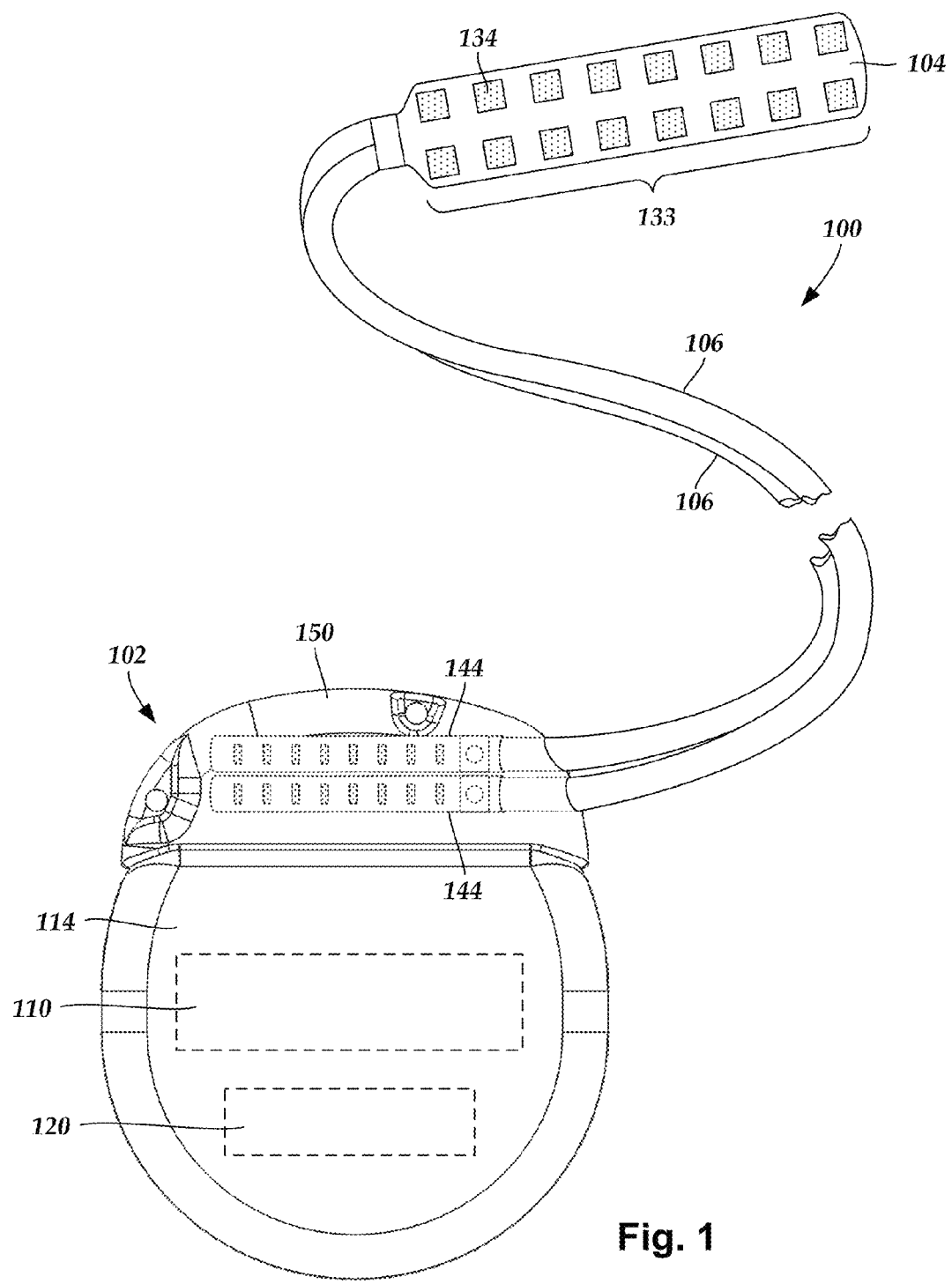
FIG. 1 is a schematic view of one embodiment of an electrical stimulation system that includes a paddle body coupled to a control module via lead bodies, according to the invention.

The present invention is directed to the area of implantable electrical stimulation systems and methods of making and using the systems. The present invention is also directed to implantable electrical stimulation systems having improved connector assembly designs, as well as methods of making and using the connector assemblies and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Electrical stimulation systems can be used to stimulation patient tissue in many different regions of a patient's body and may include, for example, spinal cord stimulation, peripheral nerve stimulation, deep brain stimulation, and the like. In the case of deep brain stimulation, a lead may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Pat. No. 8,600,518 ("Electrodes For Stimulation Leads and Methods of Manufacture and Use"), U.S. Pat. No. 8,473,061 ("Deep Brain Stimulation Current Steering with Split Electrodes"), and U.S. Patent Application Publication No. 2009/0187222. Each of these references is incorporated herein by reference in its respective entirety.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contact (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
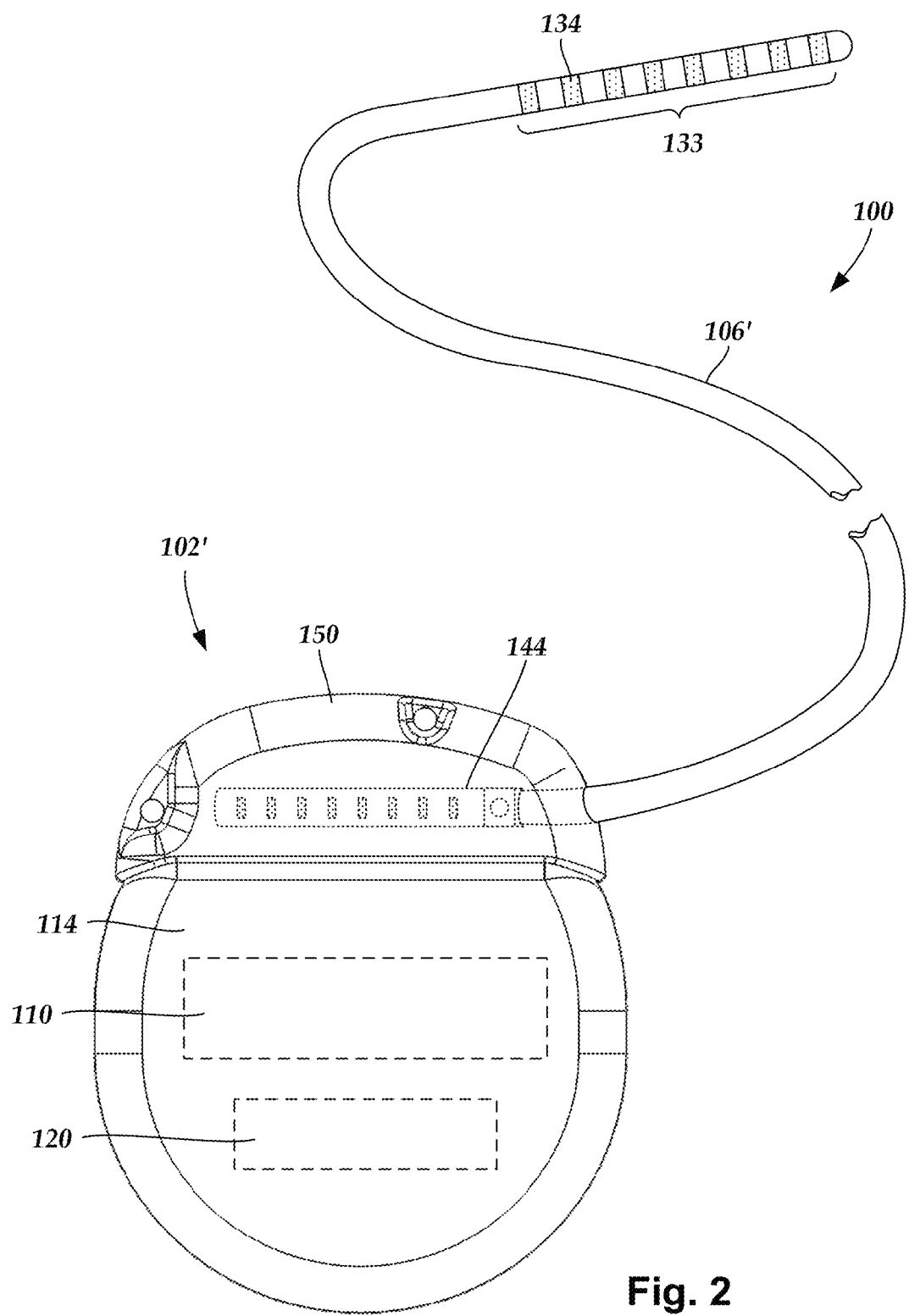
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
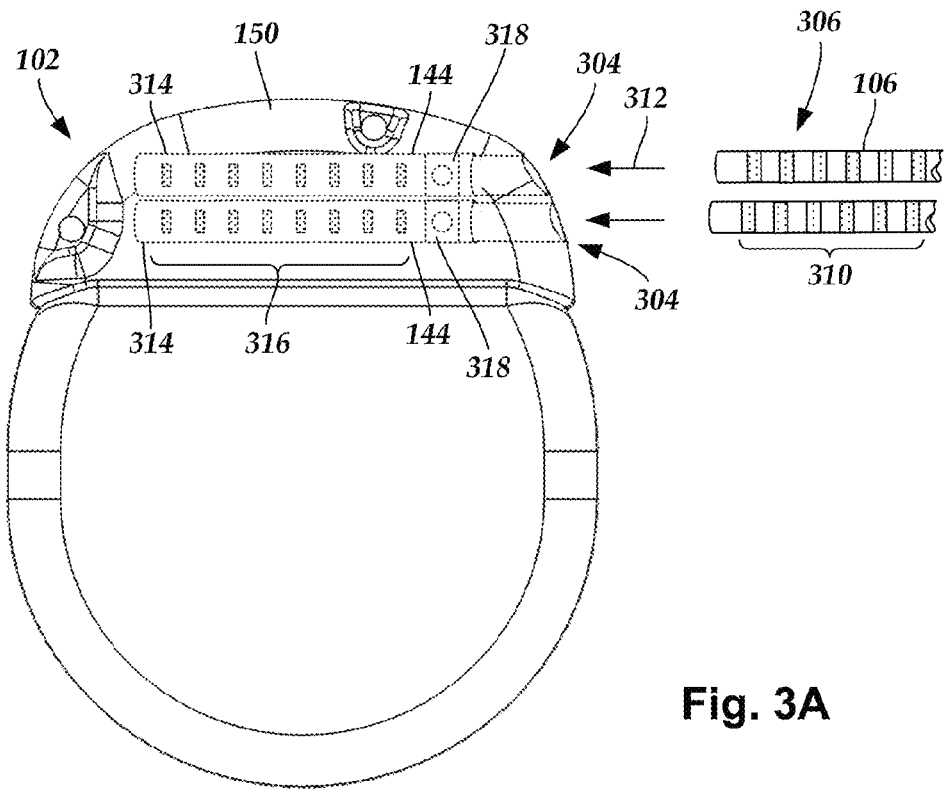
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
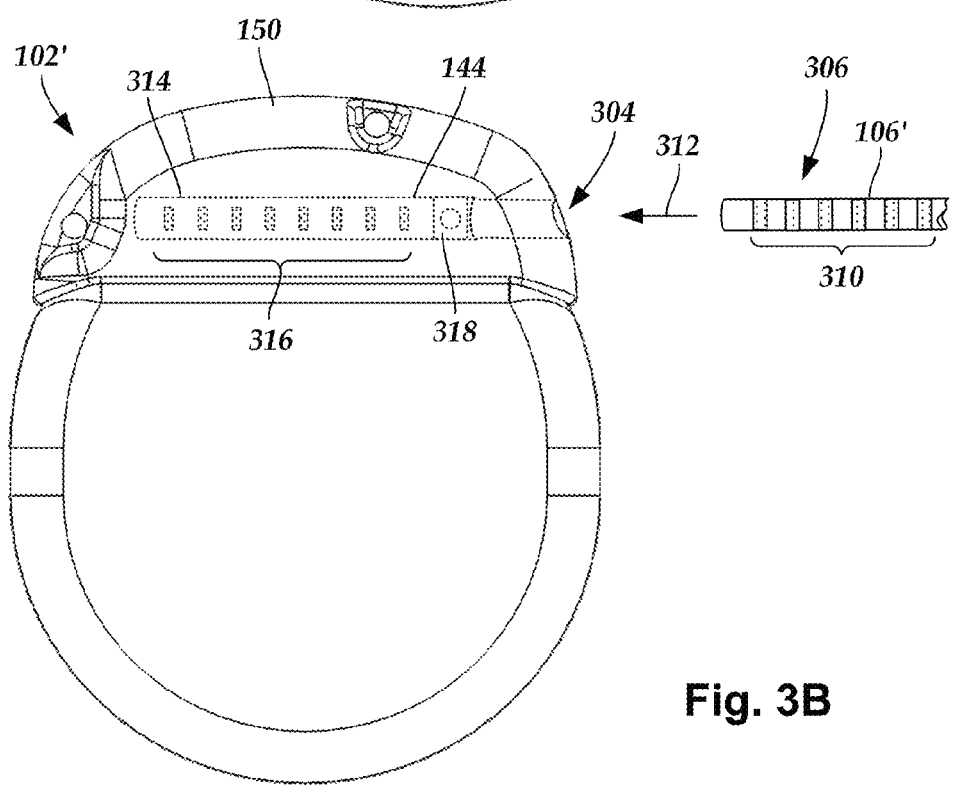
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
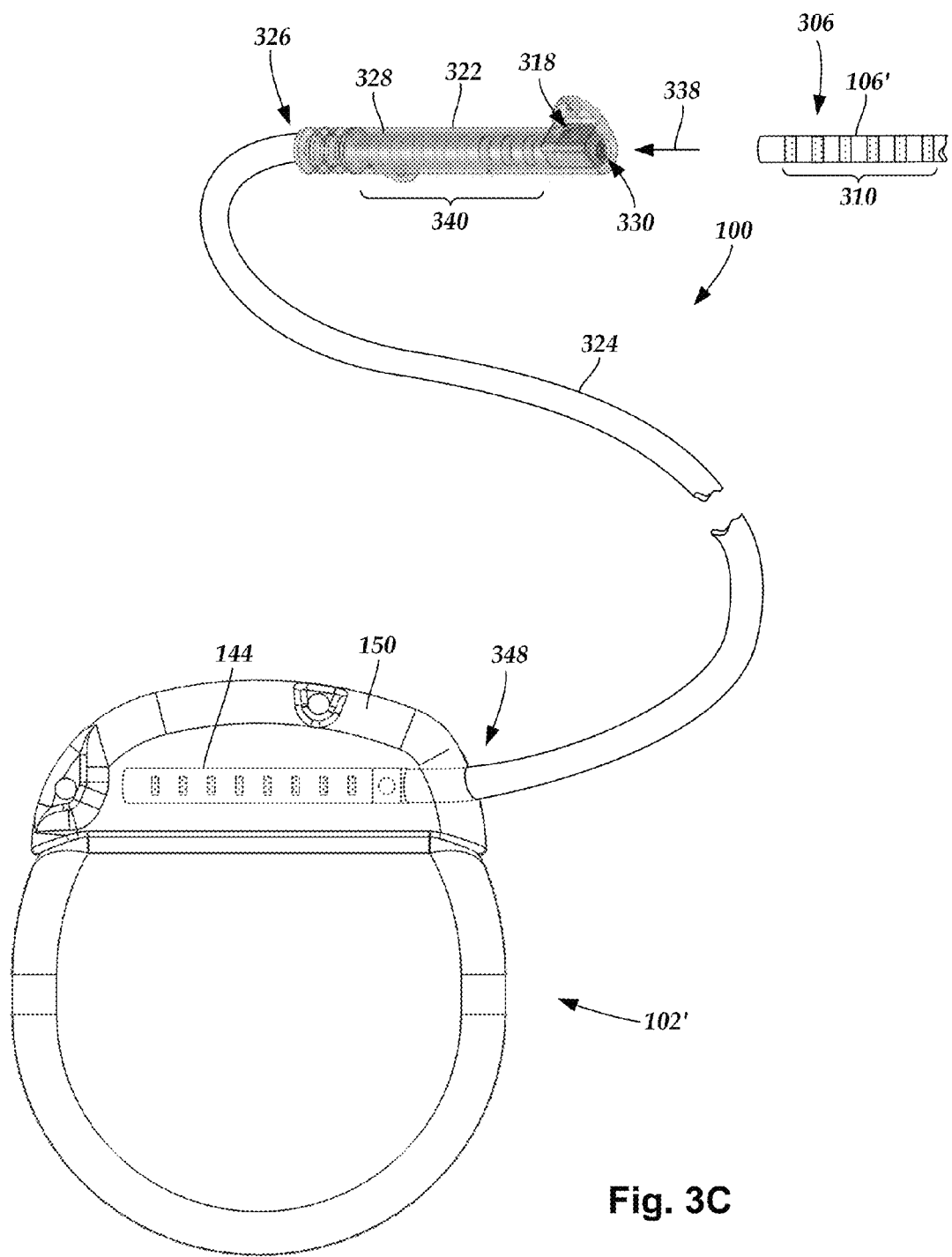
FIG. 3C is a schematic view of one embodiment of a proximal portion of the lead body of FIG. 2, a lead extension with a lead extension connector assembly, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a connector housing 328. The connector housing 328 defines at least one port 330 into which a proximal end 306 of the lead body 106' with terminals 310 can be inserted, as shown by directional arrow 338.

The lead extension connector assembly 322 also includes a plurality of connector contact housings 340. At least one connector contact 316 is disposed on, or in, each of the connector contact housings 340 such that, when the lead body 106' is inserted into the port 330, the connector contacts 316 can be aligned with the terminals 310 on the lead body 106' to electrically couple the lead extension 324 to the electrodes (134 of FIG. 1) disposed at a distal end (not shown) of the lead body 106'. The lead extension connector assembly 322 may also include the retaining element 318 for retaining the lead body 106' when the lead body 106' is inserted into the port 330.

The proximal end of a lead extension can be similarly configured and arranged as a proximal end of a lead body. The lead extension 324 may include a plurality of conductive wires (not shown) that electrically couple the connector contacts to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A. In some cases, two or more lead extensions 324 may be coupled together. In which case, the at least one port 330 may receive the proximal end of another lead extension 324.

Patient movement may eventually cause a lead or lead extension inserted into a connector to loosen, or even disconnect, from the connector assembly, thereby reducing, or even completely discontinuing, the therapeutic effects of the electrical stimulation system. For example, loosening of the lead or lead extension within the connector assembly may cause terminals of the lead or lead extension to become partially, or even fully, misaligned with connector contacts disposed in the connector assembly. It may, therefore, be advantageous to form a connector assembly such that an inserted lead or lead extension is more likely to remain inserted into the connector assembly despite bending, twisting, and stretching caused by patient movement over time.

When a lead or lead extension is inserted into a conventional connector assembly, there may not be any feedback provided to the medical practitioner for gauging the degree of insertion of the lead or lead extension into the port of the connector assembly. Consequently, a lead or lead extension may be inserted into the connector assembly such that the lead or lead extension appears to be properly inserted, yet terminals of the lead or lead extension are, in fact, not fully contacting conductive contacts of the connector assembly. In such cases, the connector assembly and the lead or lead extension may be more likely to loosen or disconnect from one another over time. It may, therefore, be advantageous to form a connector assembly that enables a medical practitioner to more easily identify when a lead or lead extension is fully inserted into the connector assembly. It may further be advantageous to form a connector assembly that enables a medical practitioner to identify when terminals of a lead or lead extension are aligned with connector contacts of the connector assembly as the lead or lead extension is inserted into the connector assembly. It may also be advantageous to form a connector assembly with connector contacts that increase the likelihood of maintaining contact with terminals of an inserted lead or lead extension, despite small misalignments.

In the case of lead extension connector assemblies, it may also be useful to provide the lead extension with a connector assembly having a transverse diameter that is smaller than conventional lead extension connector assemblies. It may also be useful to provide a lead extension with a contact housing that is isodiametric, or nearly isodiametric.

In the case of deep brain stimulation, lead extension connectors are typically disposed over the patient's skull. In which case, patient skin disposed over conventional lead extensions (and in particular over conventional lead-extension connectors) may begin to erode due to the size of connectors assembly extending outwards from the patient's skull, the tightness of skin over the connector, and the potential mobility (e.g., rotational, translational, or the like) of the conventional lead extensions relative to the patient during patient activity. Additionally, the mobility of conventional lead extensions relative to patient movement may also cause lead extension failure (e.g., electrical disconnection). One technique that has previously been used for reducing these adverse effects is to carve out portions of the patient's scalp or skull to form one or more recesses; position the connector assembly or one or more portions of the lead extension in the one or more recesses; and suture the connector or lead extension to surrounding periosteom or scalp tissue. Carving out one or more recesses, however, can be labor intensive and invasive.

As herein described, a connector assembly includes a plurality of connector contacts that improve alignment between the connector contacts and inserted terminals. The connector assemblies have reduced-profile transverse diameters from conventional connector assemblies. The connector contacts are disposed on a connector contact unit. The connector contact unit can include either a connector contact housing or a connector coupler.

In some instances, the connector assembly may additionally include one or more of the following: a strain relief arrangement, an end stop, one or more windows through which a medical practitioner can view a portion of a lead or lead extension while inserted into a connector assembly, a retaining element, or one or more connector flanges. In the case of connector couplers, the connector coupler can be used to mechanically couple with an inserted lead or lead extension in addition to, or in lieu of, electrically coupling connector contacts with the inserted lead or lead extension. For example, the connector coupler can be used as an end stop.

It will be understood that the connector assembly may be disposed in many different locations including, for example, on lead extensions (see e.g., 322 of FIG. 3C), lead adapters, lead splitters, the connector portion of control modules (see e.g., 144 of FIGS. 1-3B), or the like. In preferred embodiments, the connector assemblies are disposed on the distal ends of lead extensions, as described in more detail below. It will be understood that, depending on the location of the connector assembly, one or more components of the connector assembly may be omitted. For example, connector assemblies disposed on control modules typically do not include strain relief arrangements.

Figure 4:
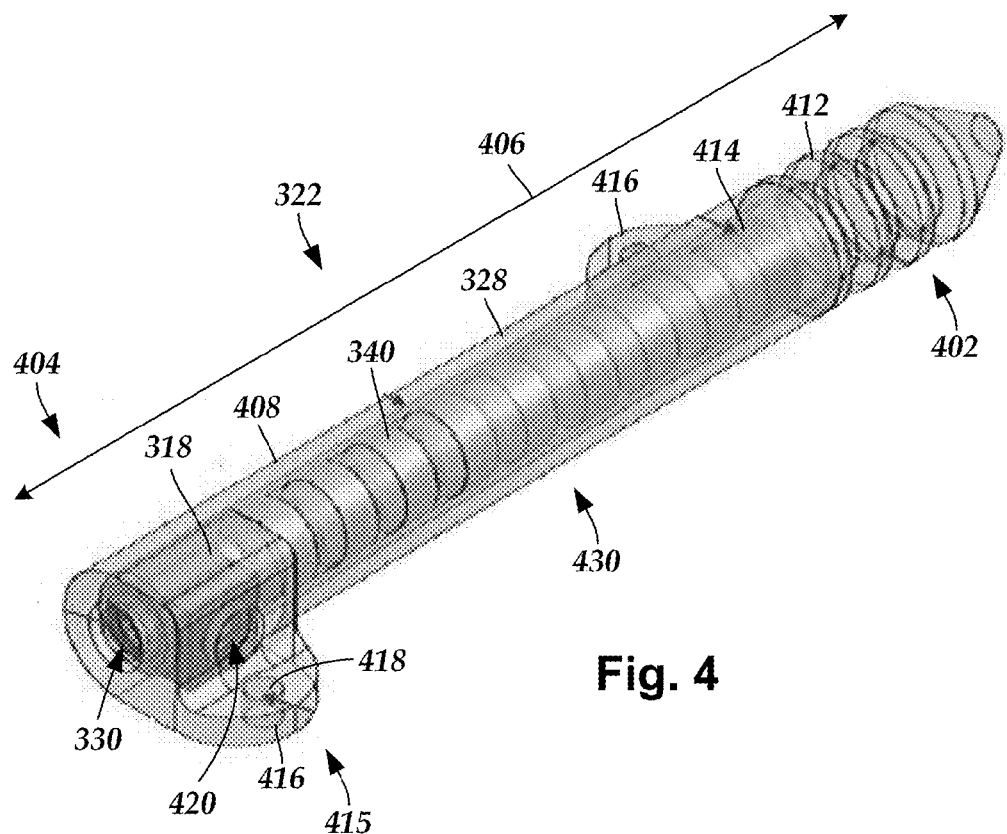
FIG. 4 is a schematic perspective view of one embodiment of the lead extension connector assembly of FIG. 3C; according to the invention.

FIG. 4 is a schematic perspective view of one embodiment of the connector assembly 322. The connector assembly 322 has a first end 402, a second end 404, and a length 406, shown in FIG. 4A as a two-headed arrow. The connector assembly 322 includes the connector housing 328. The connector housing 328 defines a port 330 into which a proximal end of a lead or lead extension can be inserted. In alternate embodiments, the connector housing 328 includes two or more ports, each configured and arranged to receive a portion of a lead, or a lead extension, or both (see e.g., FIGS. 1 and 3A).

The port 330 opens into a lumen (512 in FIGS. 5A-5C) extending along at least a portion of the length 406 of the connector assembly 322. A plurality of connector contacts 316 are disposed in the lumen such that the connector contacts 316 are electrically coupleable with leads or lead extensions inserted into the port 330. The connector contacts are disposed in connector contact units 430. In at least some embodiments, the connector contact units 430 include axially-spaced-apart connector contact housings, such as contact housing 340, disposed in the lumen. In other embodiments (see e.g., FIGS. 8A-11), the connector contact units 430 include connector couplers (802 in FIG. 8A) disposed in the lumen.

In some cases, material 408 may be disposed over at least a portion of the connector housing 328. Optionally, the material 408 may be transparent or translucent to form windows through which a practitioner can view one or more portions of the lead or lead extension when the lead or lead extension is inserted in the port 330. The material 408 can be formed from any suitable biocompatible material (e.g., polycarbonate, or the like).

The connector assembly 322 may, optionally, include one or more strain relief arrangements 412 disposed along at least one portion of the connector assembly 322. The strain relief arrangement 412 is configured and arranged to expand and contract along the length 406 to absorb strain potentially placed on the connector assembly 322 by patient movement. In some cases, the one or more strain relief arrangements 412 can bend with respect to a longitudinal axis of the connector assembly 322. In at least some embodiments, at least one of the one or more strain relief arrangements 412 is disposed at the first end 402 of the connector assembly 322. The strain relief arrangement 412, optionally, can be formed as a portion of the connector housing 328.

The connector assembly 322 may include an end stop 414 which, at least in part, modulates insertion of the lead or lead extension into the port 330. The end stop 414 can be disposed in the lumen of the connector assembly 322 in proximity to the first end 402. The end stop 414 can provide one or more surfaces upon which the inserted lead or lead extension contacts, when the lead or lead extension is fully inserted into the port 330. In some cases, the end stop 414 can provide the proximal-most point of insertion for the lead or lead extension within the connector assembly 322.

In some cases, it may be useful to provide one or more anchoring units 415 for anchoring the connector assembly 322 to patient tissue. For example, in the case where the connector assembly 322 is disposed on a lead extension used for deep brain stimulation, one or more anchoring units 415 may be coupled to one or more surfaces of the connector assembly and be used to couple the connector assembly 322 to the patient's skull (e.g., using one or more fasteners, such as bolts, screws, pins, or the like, that extend through the anchoring unit 415). The one or more anchoring units may stabilize the orientation of the connector assembly 322, such as preventing the connector from rotating about a longitudinal length of the connector assembly 322.

At least some conventional connector assemblies are configured to be anchored to patient tissue by suturing the connector housing directly to patient tissue. Suturing a connector assembly directly to patient tissue can potentially cause damage to a corresponding lead extension or lead. In some instances, the one or more anchoring units 415 provide a surface for securing the connector assembly to the patient without suturing the connector housing directly to patient tissue.

One example of an anchoring unit 415 is a connector flange 416. One or more connector flanges 416 can be disposed on any external surface of the connector assembly 322. In some cases, the connector flange 416 extends tangentially from the connector assembly 322. The connector flange 416 may define one or more connecting apertures 418 through which a fastener (e.g., a screw, pin, suture, binding clip, or the like) may be inserted and secured against patient tissue. Optionally, the connector flange 416 may include a surface that is configured and arranged for promoting tissue ingrowth (e.g., via appropriately sized and shaped recesses, or the like). The tissue ingrowth may facilitate securing of the anchoring unit 415 to patient tissue over the implantable lifetime of the connector assembly 322.

In some cases, the connector assembly 322 includes the retaining element 318, which is configured and arranged to retain the lead or lead extension within the connector assembly 322. The retaining element 318 defines an aperture 420 through which a fastener (e.g., a set screw, pin, or the like) may be inserted and secured against an inserted lead or lead extension. When the connector assembly 322 includes one or more connector flanges 416, it may be advantageous to configure the retaining element 318 such that the aperture 420 extends parallel with at least one of the connector flanges 416. Such an arrangement may reduce the profile of the connector assembly 322 along an axis perpendicular to the axis along which the aperture 420 and the connector flange 416 extend. This may be of a particular advantage when the connector assembly 322 is disposed on a lead extension used for deep brain stimulation. In which case, the connector assembly 322 may facilitate a reduction of skin erosion by taking advantage of the anatomy of the region of implantation where, although the tightness of patient skin discourages the connector assemblies from extending very far outward from the patient's skull, there is often ample space to extend the connector assemblies outward along the surface of the patient's skull.

Figure 5A:
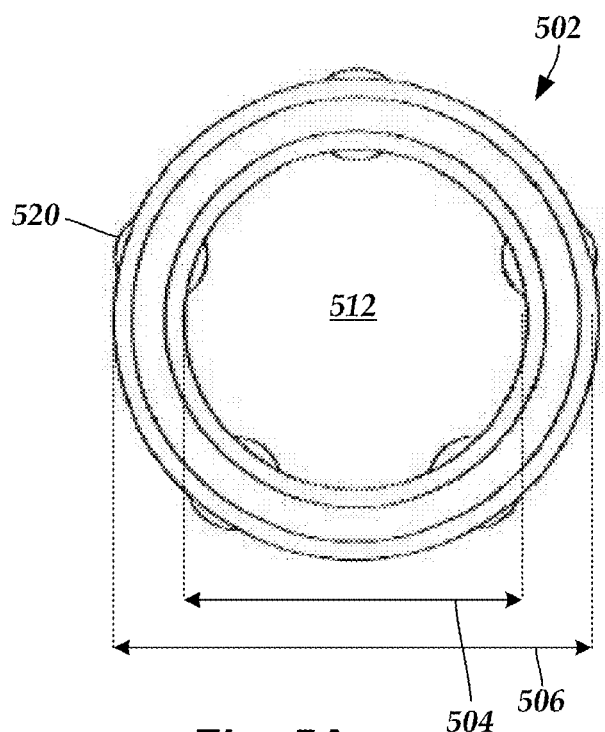
FIG. 5A is a schematic top view of one embodiment of connector contacts disposed on a connector contact housing suitable for use with the connector assembly of FIG. 4, according to the invention.

Turning to FIG. 5A, in some cases the connector assembly 322 includes connector contact housings. In which case, at least one connector contact (e.g., 316 in FIGS. 3A and 3B) is disposed on, or in, each of the connector contact housings (e.g., 340 in FIGS. 3C and 4). FIG. 5A through FIG. 7 illustrate several different embodiments of connector contacts disposed on or in connector contact housings.

Figure 5B:
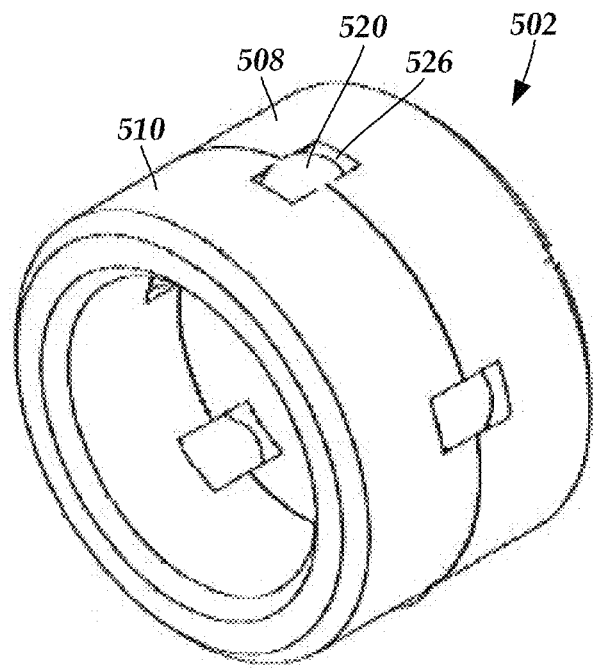
FIG. 5B is a schematic perspective view of one embodiment of the connector contact housing of FIG. 5A, according to the invention.
Figure 5C:
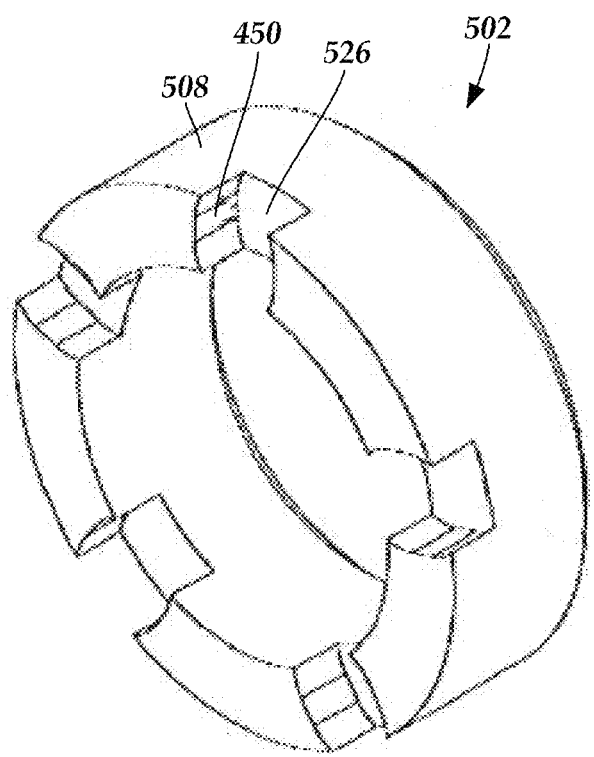
FIG. 5C is a schematic perspective cross-sectional view of one embodiment of the connector contact housing of FIG. 5A without the connector contacts of FIG. 5A, according to the invention.

FIG. 5A is a schematic front view of one embodiment of a connector contact housing 502. FIG. 5B is a schematic perspective view of the connector contact housing 502. FIG. 5C is a schematic perspective cross-sectional view of a portion of the connector contact housing 502. In this embodiment, the connector contact housing 502 is substantially cylindrical with an inner diameter 504 and an outer diameter 506. In some cases, the connector contact housing 502 includes multiple elements 508, 510 axially coupled together. The inner diameter 504 of the connector contact housing 502 defines a portion of a lumen 512. As discussed above, with reference to FIG. 4, the lumen is continuous with the port 330 and extends along at least a portion of the length 406 of the connector assembly 322.

A plurality of connector contacts 520 are disposed on or in the connector contact housing 502 such that a portion of each connector contact 520 is exposed to the lumen 512. By exposing the connector contacts 520 to the lumen 512, the connector contacts 520 can electrically couple with a terminal of a lead or lead extension when a terminal-containing end of the lead or lead extension is inserted into the port 330. For each particular connector contact housing 502, the connector contacts 520 each form a separate contact point between at least one (in at least some embodiments, only one) terminal of the inserted lead or lead extension and the electrical subassembly (110 in FIG. 1). It may be advantageous to establish a plurality of contact points between a terminal and the connector assembly 332 to reduce the risk of electrical misalignment between the terminal and the connector contacts 520. The connector contacts 520 are electrically coupled to the electrical subassembly (110 in FIG. 1). In some cases, each of the connector contacts 520 may be electrically coupled to one another via one or more conductive portions of the connector contact housing 502.

The connector contact housings 502 can be configured and arranged to be coupled together into a stack. In which case, the connector contact housings 502 can be stacked such that for each connector contact housing 502 the connector contacts 520 of that connector contact housing 502 couple with a first terminal of an inserted lead or lead extension, while the connector contacts of another connector contact housing couple with a second terminal, and so on.

In some instances, the connector contacts 520 are disposed in pockets 526 that are defined in the connector contact housing 502 and that open along the inner diameter 504. In at least some embodiments, each pocket 526 is configured and arranged to receive and retain a single connector contact 520. In alternate embodiments, the pockets 526 are configured and arranged to receive and retain a plurality of connector contacts 520 (see e.g., FIG. 7). In some instances, at least a portion of the pockets 526 is formed from a conductive material and makes an electrical connection with one or more connector contacts 520. When the connector contact housing 502 includes multiple elements 508, 510, the pockets 526 may be formed such that a portion of at least one of the pockets 526 is defined in each of the elements 508, 510 such that, when the elements 508, 510 are coupled together, partial pockets 526 on each of the elements 508, 510 collectively form a complete pocket 526.

The connector contacts 520 can be formed in any suitable shape. In preferred embodiments, the connector contacts 520 are spherical. The pockets 526, optionally, can be formed to enable the connector contacts 520 to retract (e.g., move radially outward with respect to the lumen 512) upon contact with an inserted lead or lead extension. FIG. 5C shows an extended portion 450 of the pockets 526 that extends the pocket 526 along a radial axis. In preferred embodiments, the connector contacts 520 can retract enough to reduce the amount of force needed to insert the lead or lead extension into the port 330, while still maintaining electrical contact with the inserted lead or lead extension. Decreasing the amount of force needed to insert the lead or lead extension may reduce damage to the lead, lead extension, or connector assembly 502 caused as a result of excessive force being applied to the lead or lead extension during insertion of the lead or lead extension into the port 330.

In some cases, the pockets 526 are open to the outer diameter 506 of the connector contact housing 502. In which case, the connector contacts 520 may extend radially from the outer diameter 506 of the connector contact housings 502. When the material 408 is disposed over at least a portion of the connector housing 328, the outermost portions of the connector contacts 520 may contact the material 408. The material 408 may have elastic properties suitable for providing an inward radial force against the connector contacts 520 that may be used to maintain contact between the connector contacts 520 and an inserted lead or lead extension.

Figure 6:
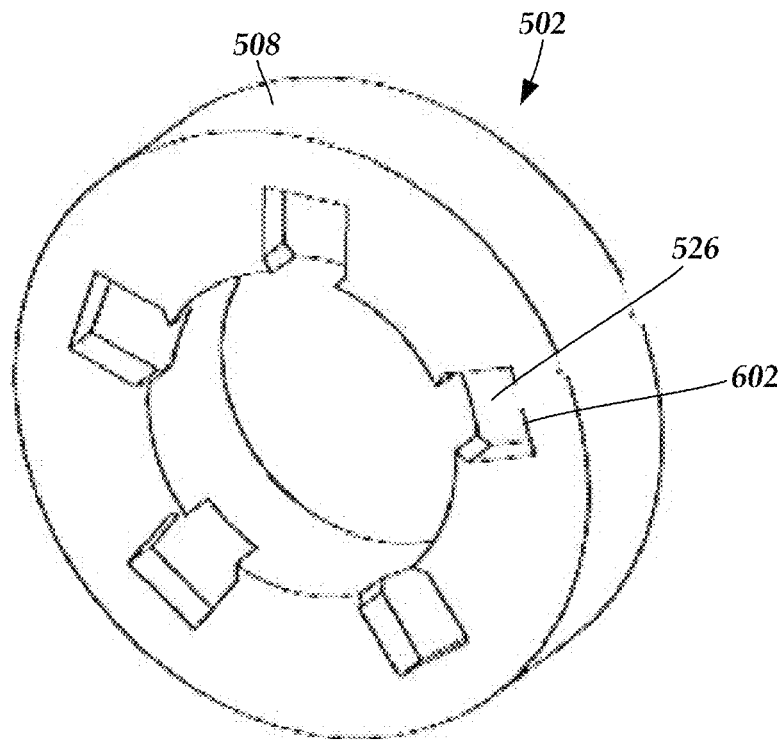
FIG. 6 is a schematic perspective cross-sectional view of another embodiment of the connector contact housing of FIG. 5A without the connector contacts of FIG. 5A, according to the invention.

Turning to FIG. 6, in alternate embodiments the pockets 526 do not extend to the outer diameter 506 of the connector contact housing 502. FIG. 6 is a schematic perspective cross-sectional view of one embodiment of the element 508 of the connector contact housing 502. In FIG. 6, the pockets 526 defined in the element 508 do not extend to the outer diameter 506 of the connector contact housing 502. In which case, an outward-most surface 602 along a radial axis can provide an inward radial force against the connector contacts 520 (not shown in FIG. 6 for clarity of illustration) that may be used to maintain contact between the connector contacts 520 and an inserted lead or lead extension.

Figure 7:
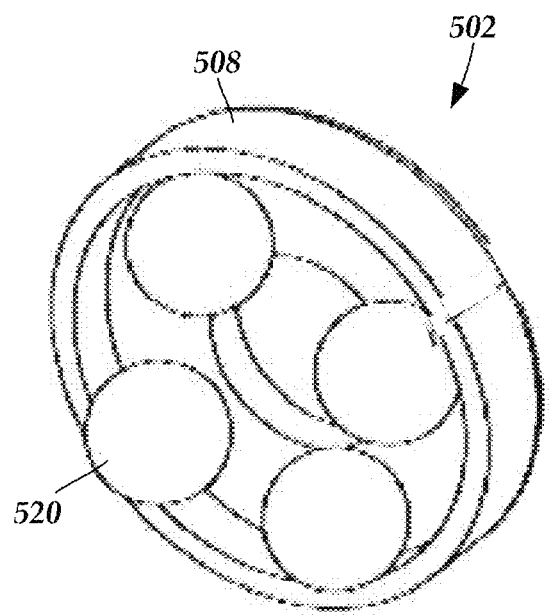
FIG. 7 is a schematic perspective cross-sectional view of yet another embodiment of the connector contact housing of FIG. 5C with the connector contacts of FIG. 5A, according to the invention.

Turning to FIG. 7, in alternate embodiments at least one of the connector contact housings 502 is configured and arranged to receive more than one connector contact 520. In at least some embodiments, the connector contact housing 502 defines a single pocket 526 that contains a plurality of the connector contacts 520. FIG. 7 is a schematic perspective cross-sectional view of one embodiment of the element 508 of the connector contact housing 502. The connector contact housing 502 defines a single pocket 526 configured and arranged to contain each of the connector contacts 520. Optionally, the connector contacts 520 may be able to move freely within the pocket 526. When the connector contact housing 502 includes multiple elements, 508, 510, the pocket 526 can be defined in either element 508 or 510, or collectively in both elements 508, 510 (as described above, with reference to FIGS. 5A-5C). Note that the embodiment of the connector contact housing 502 illustrated in FIG. 7 includes a pocket 526 that is defined in both elements 508, 510. Element 510, however, is not shown in FIG. 7 for clarity of illustration.

Figure 8A:
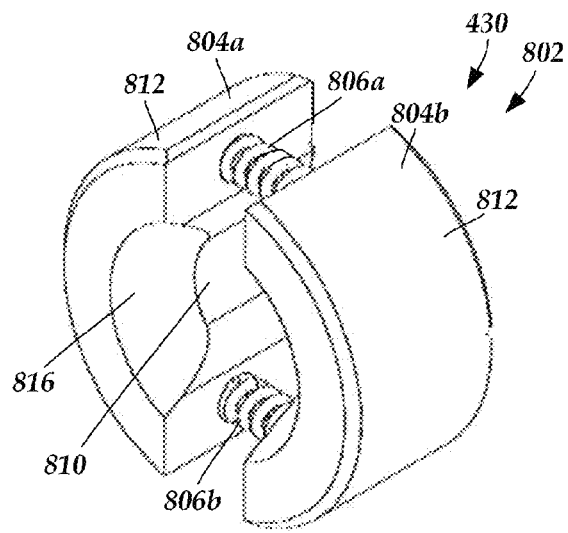
FIG. 8A is a schematic perspective view of one embodiment of a connector coupler having coupling members coupled together by elastic members, the elastic members formed as coiled springs, according to the invention.

Turning now to FIG. 8A, in some cases connector contacts are disposed in connector contact units formed as connector couplers. FIGS. 8A-11 illustrate several different exemplary embodiments of connector couplers.

FIG. 8A is a schematic perspective view of one embodiment of connector contact unit 430 formed as a connector coupler 802. The connector coupler 802 includes a plurality of coupling members 804a and 804b attached to one another by elastic members 806a and 806b. In FIG. 8, the connector coupler 802 is shown having two coupling members 804a and 804b attached to one another on opposite ends by two elastic members 806a and 806b. The connector coupler 802, however, can include any suitable number of coupling members including, for example, two, three, four, five, six, or more coupling members. The connector coupler 802 can include any suitable number of elastic members including, for example, two, three, four, five, six, or more elastic members. The number of coupling members can be less than, equal to, or greater than the number of elastic members.

The coupling members 804a and 804b include inner surfaces 810 and outer surfaces 812. In at least some embodiments, the inner surfaces 810 form concave arcs. The outer surfaces 812 can be formed in any suitable shape. In at least some embodiments, the outer surfaces 812 are likewise arced. When the connector coupler 802 has two coupling members 804a and 804b, the inner surfaces 810 may be formed as opposing C-shapes. The inner surfaces 810 are configured and arranged to contact an outer surface of a lead or lead extension inserted into the port 330. In some cases, the inner surfaces 810 are configured and arranged to contact a terminal of an inserted lead or lead extension.

The connector coupler 802 can be used to couple with an inserted lead or lead extension either mechanically, electrically, or both. When a mechanical connection is desired with an inserted lead or lead connection, the inner surfaces 810 of the coupling members 804a and 804b can be formed from either conductive or non-conductive, biocompatible material(s) suitable for implantation. When an electrical connection is desired with the inserted lead or lead extension, the connector contacts can be formed from the inner surfaces 810 of the coupling members 804 and 804b. In which case, the inner surfaces 810 are conductive. Alternately, connector contacts can be formed from one or more conductive members (e.g., conductive beads, or the like) coupled to the inner surfaces 810. In which case, the inner surfaces 810 can be formed from either conductive or non-conductive, biocompatible material(s) suitable for implantation.

As mentioned above, the connector coupler 802 can be used to mechanically couple to an inserted lead or lead extension in addition to, or in lieu of, electrically coupling to the lead or lead extension. FIGS. 8A-11 illustrate embodiments of the connector coupler 802 for use as connector contacts. It will be understood that the connector coupler 802 can also be used to establish a desired mechanical connection with an inserted lead in addition to, or in lieu of, an electrical connection. For example, the connector coupler 802 can be used to form the end stop 414 to modulate insertion of the lead or lead extension into the connector assembly 322.

In FIG. 8A, the elastic members 806a and 806b are shown as being coiled springs. Alternately, the elastic members 806a and 806b can be formed using any suitable elastic structure (e.g., one or more bands, cords, clips, sleeves, or the like) formed from any suitable biocompatible material.

Figure 8B:
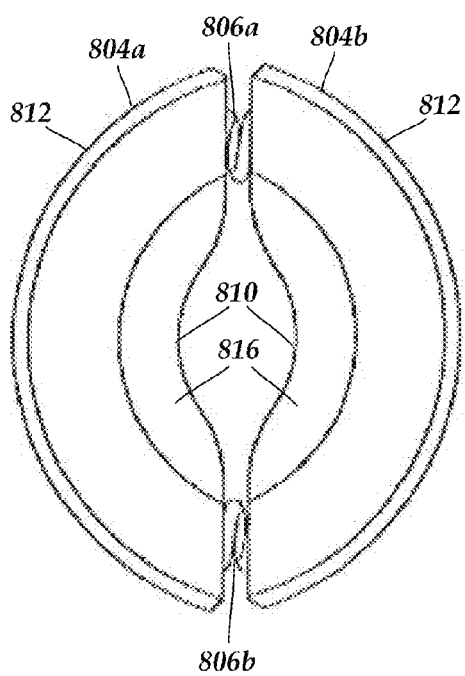
FIG. 8B is a schematic front view of one embodiment of the connector coupler of FIG. 8A, the connector coupler including elastic members in a relaxed state, according to the invention.
Figure 8C:
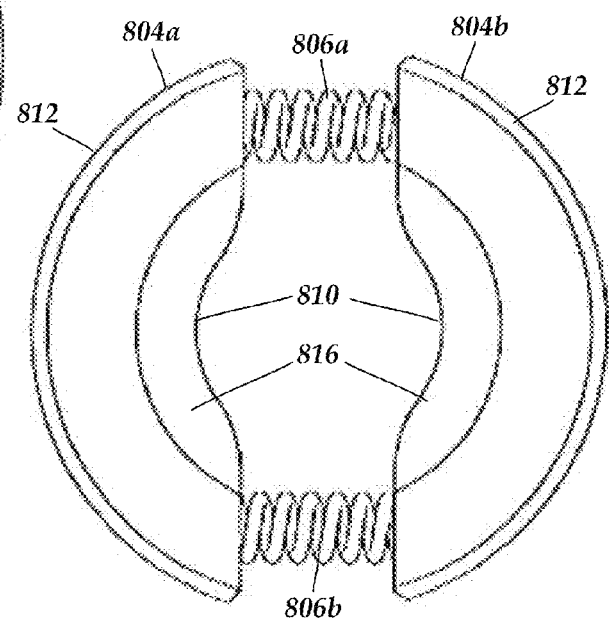
FIG. 8C is a schematic front view of one embodiment of the connector coupler of FIG. 8A, the connector coupler including elastic members in an expanded state, according to the invention.

The elastic members 806a and 806b can be used to maintain a connection between the coupling members 804a and 804b and an inserted lead or lead extension. FIG. 8B is a schematic front view of one embodiment of the connector coupler 802 with the elastic members 806a and 806b in a relaxed state. FIG. 8C is a schematic front view of one embodiment of the connector coupler 802 with the elastic members 806a and 806b in an expanded state. In some instances, the elastic members 806a and 806b can be formed such that the coupling members 804a and 804b are held in close proximity to one another when in a relaxed state. It may be advantageous for the elastic members to hold the coupling members in close proximity to one another when in a relaxed state to potentially reduce the transverse profile of the connector assembly when a lead or lead extension is not disposed in the connector assembly 322. In at least some embodiments, when the elastic members 806a and 806b are in a relaxed state, the distance between the coupling members 804a and 804b is less than a diameter of the inserted lead or lead extension.

The force constant of the elastic members 806a and 806b can be used to adjust the amount of force needed to expand the elastic members 806a and 806b enough to be able to insert a lead or lead extension between the inner surfaces 810 of the coupling members 804a and 804b. Once the lead or lead extension is inserted between the coupling members 804a and 804b, the force constant also controls how tightly the coupling members 804a and 804b remain coupled to the inserted lead or lead extension. Optionally, the amount of force needed to insert the lead or lead extension between the coupling members 804a and 804b can be further adjusted by providing a chamfered surface 816 along at least a portion of one side of one of the inner surfaces 810 of the connector coupler 802 to reduce the amount of applied force needed to insert a lead or lead extension between the coupling members 804a and 804b.

Figure 9A:
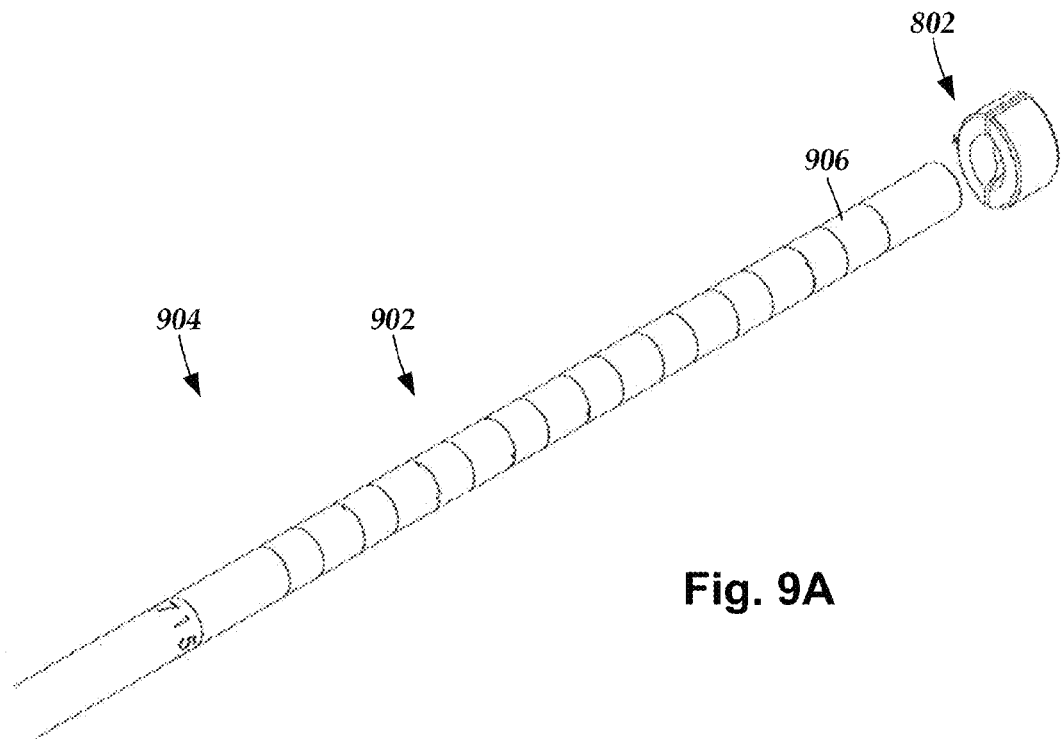
FIG. 9A is a schematic perspective view of one embodiment of the connector coupler of FIG. 8A configured and arranged for coupling to a proximal end of a lead or lead extension, the connector coupler including elastic members in a relaxed state, according to the invention.
Figure 9B:
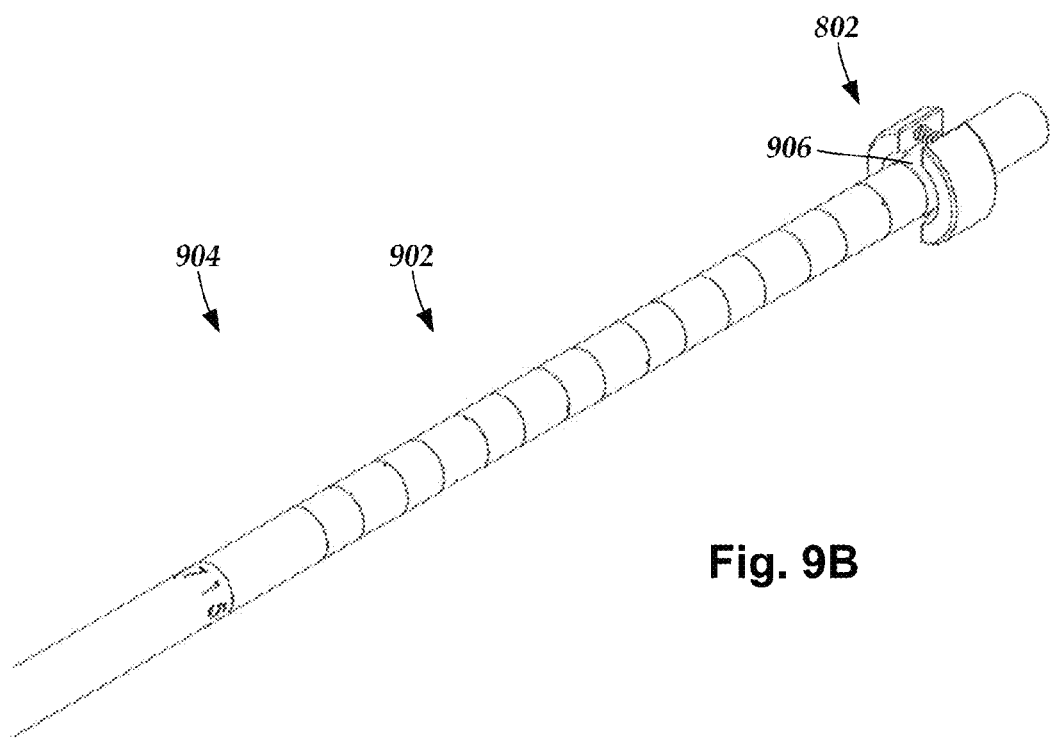
FIG. 9B is a schematic perspective view of one embodiment of the connector coupler of FIG. 8A coupled to a proximal end of the lead or lead extension of FIG. 9A, the connector coupler including elastic members in an expanded state to receive the lead or lead extension, according to the invention.

FIG. 9A is a schematic perspective view of one embodiment of the connector coupler 802 positioned in proximity to a proximal end 902 of a lead or lead extension 904. The elastic members 806a and 806b of the connector coupler 802 are in relaxed states. FIG. 9B is a schematic perspective view of one embodiment of the connector coupler 802 disposed over a terminal 906 disposed on the proximal end 902 of the lead or lead extension 904. The elastic members 806a and 806b of the connector coupler 802 are in expanded states to receive the terminal 906 of the lead or lead extension 904. In preferred embodiments, the elastic members 806a and 806b have force constants that are low enough to enable insertion of the lead or lead extension 902 between the coupling members 804a and 804b, yet high enough to remain coupled to the received terminal 906.

Figure 10:
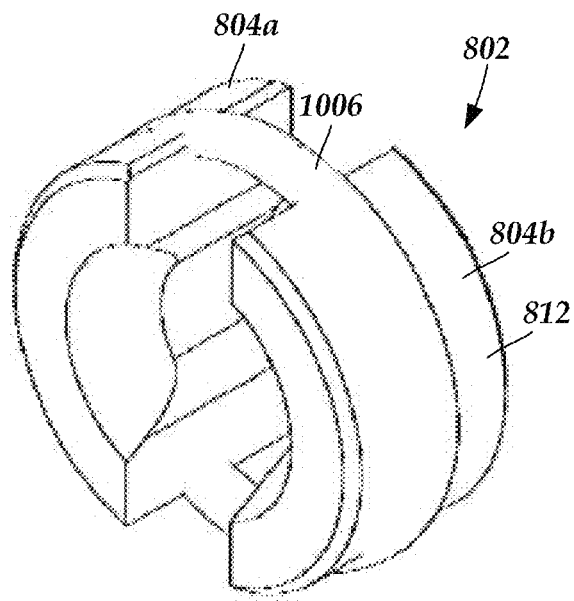
FIG. 10 is a schematic perspective view of another embodiment of the connector coupler of FIG. 8A, the connector coupler having an elastic member formed as an elastic band, according to the invention.

Turning to FIG. 10, in alternate embodiments the elastic members 806a and 806b are formed using other elastic structures in lieu of, or in addition to, coiled springs. FIG. 10 is a schematic perspective view of another embodiment of the connector coupler 802. In FIG. 10, the coupling members 804a and 804b are held together by one or more elastic bands 1006. In some cases, one or more elastic bands 1006 can be extended around a circumference of the connector coupler 802. In which case, the outer surfaces 812 may define one or more grooves (not shown) along which portions of the one or more elastic bands 1006 may extend. In some cases, the one or more grooves can be sized to receive the one or more elastic bands 1006 such that the one or more elastic bands 1006 do not extend radially outward therefrom.

Figure 11:
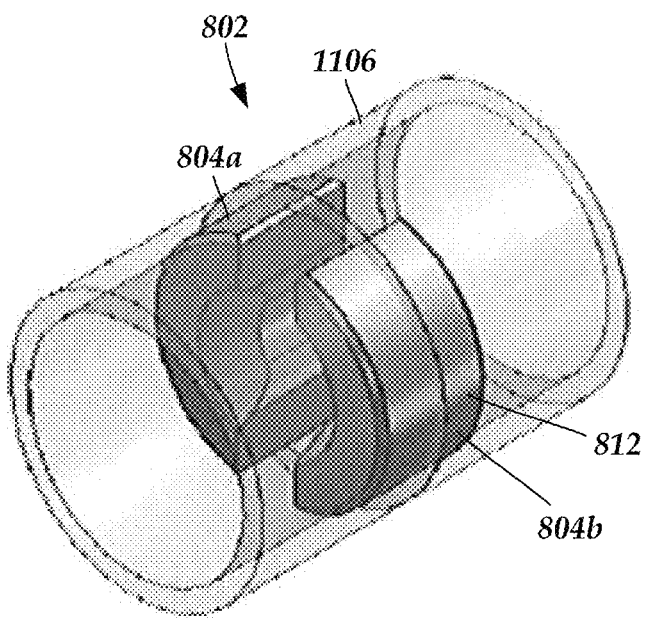
FIG. 11 is a schematic perspective view of yet another embodiment of the connector coupler of FIG. 8A, the connector coupler having coupling members coupled together by an elastic member formed as a sheath disposed over the coupling members, according to the invention.

FIG. 11 is a schematic perspective view of yet another embodiment of the connector coupler 802. In FIG. 11, the coupling members 804*a* and 804*b* are held together by an elastic sleeve 1106 extending around a circumference of the connector coupler 802. In some instances, the elastic sleeve 1106 is the material 408 disposed over at least a portion of the connector housing 328. In other instances, the elastic sleeve 1106 is separate from the material 408 and is disposed (e.g., press fit, or the like) inside the material 408.

Figure 12:
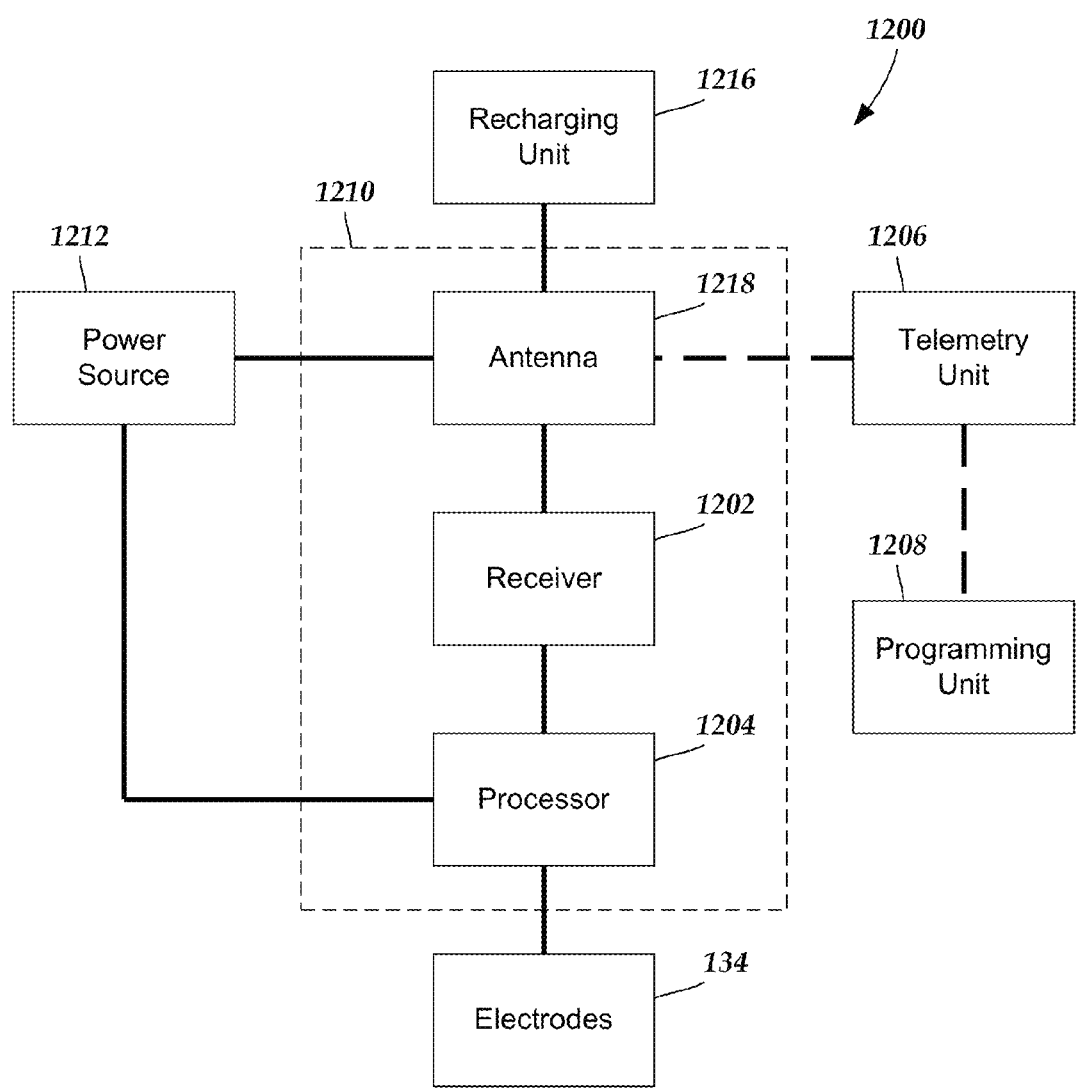
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable medical device, the connector comprising:
   an elongated connector housing having a first end, a second end, and a length, the connector housing defining a port at the second end of the connector housing, the port configured and arranged for receiving a proximal end portion of a lead or lead extension;
   a lumen that extends from the port along at least a portion of the length of the connector housing;
   a plurality of axially spaced-apart, substantially-cylindrical connector-contact housings disposed along the lumen, the plurality of connector-contact housings each having an inner diameter and an outer diameter and comprising a first housing element and a second housing element axially coupled to the first housing element, wherein for each connector-contact housing the inner diameter of that connector-contact housing forms a portion of a wall of the lumen, wherein each of the plurality of connector-contact housings defines a plurality of pockets arranged around a circumference of the connector-contact housing, wherein each of the pockets is defined, at least in part, by an axial indentation in at least one of the first housing element or the second housing element; and a plurality of spherically-shaped connector contacts disposed in each of the plurality of connector-contact housings with at least a portion of each of the plurality of connector contacts extending into the lumen, wherein at least one of the connector contacts is disposed in each of the plurality of pockets with a portion of the connector contact extending out of the pocket and a remainder of the connector contact is retained within the pocket, wherein the pocket is configured and arranged to hinder release of the connector contact from the pocket, wherein for each connector-contact housing each of the plurality of connector contacts disposed on or in that connector-contact housing is configured and arranged for coupling to a different single terminal disposed on a proximal end portion of a lead or lead extension when the proximal end portion of the lead or lead extension is inserted into the lumen.

2. The connector of claim 1, wherein each of the plurality of pockets is configured and arranged for receiving a single connector contact of the plurality of connector contacts.

3. The connector of claim 1, wherein each of the plurality of pockets is configured and arranged for receiving at least two contacts of the plurality of connector contacts.

4. The connector of claim 1, wherein each of the plurality of pockets comprises a surface that is at least partially formed from a conductive material.

5. The connector of claim 1, wherein each of the plurality of pockets is open along the inner diameter of the connector-contact housing.

6. The connector of claim 5, wherein each of the plurality of pockets is open along the outer diameter of the connector-contact housing.

7. The connector of claim 6, further comprising elastic material disposed over the connector housing with the elastic material abutting a portion of each of the plurality of pockets that is open along the outer diameter of the connector-contact housing.

8. The connector of claim 6, wherein each of the plurality of pockets open along the outer diameter of the connector-contact housing is configured and arranged for receiving the at least one connector contact of the plurality of connector contacts with a portion of the least one connector contact extending outward from the pocket beyond the outer diameter of the connector-contact housing.

9. The connector of claim 5, wherein each of the plurality of pockets does not extend to the outer diameter of the connector-contact housing.

10. The connector of claim 1, wherein at least five connector contacts are disposed on or in at least one of the plurality of connector-contact housings.

11. The connector of claim 1, further comprising a strain relief disposed along the first end of the connector housing.

12. The connector of claim 1, further comprising an end stop disposed along the first end of the connector housing.

13. A connector assembly comprising:
the connector of claim 1; and
a lead configured and arranged for insertion into the lumen of the connector, the lead comprising
a lead body with a proximal end portion and a distal end portion,
a plurality of electrodes disposed along the distal end portion of the lead body,
a plurality of terminals disposed along the proximal end portion of the lead body, and
a plurality of conductors electrically coupling the plurality of electrodes to the plurality of terminals.

14. The connector assembly of claim 13, further comprising at least one connector flange extending outwardly tangentially from an outer surface of the connector housing of the connector, the at least one connector flange configured and arranged for providing a surface for coupling the connector assembly to patient tissue.

15. The connector assembly of claim 14, further comprising a retaining element for retaining the proximal end portion of the lead body when the proximal end portion of the lead body is inserted into the lumen, the retaining element defining an aperture configured and arranged to receive a fastener for coupling to the inserted lead body, wherein the aperture extends in a direction that is parallel to the at least one connector flange.

16. The connector assembly of claim 14, wherein the at least one connector flange defines at least one connector aperture extending completely through the at least one connector flange, the at least one connector aperture configured and arranged for receiving a fastener.

17. The connector assembly of claim 14, wherein the at least one connector flange comprises at least one surface that defines at least one recess configured and arranged for promoting tissue ingrowth.

18. An electrical stimulating system comprising:
a lead comprising
a lead body with a proximal end portion and a distal end portion,
a plurality of electrodes disposed along the distal end portion of the lead body,
a plurality of terminals disposed along the proximal end portion of the lead body, and
a plurality of conductors electrically coupling the plurality of electrodes to the plurality of terminals;
a control module electrically coupled to the plurality of electrodes, the control module comprising
a housing, and
an electronic subassembly disposed in the housing;
a lead extension having a proximal end portion and a distal end portion, wherein the proximal end portion of the lead extension is coupleable with the control module; and
the connector of claim 1 disposed along the distal end portion of the lead extension;
wherein the proximal end portion of the lead body is configured and arranged for insertion into the port of the connector.

19. An electrical stimulating system comprising:
a lead comprising
a lead body with a proximal end portion and a distal end portion,
a plurality of electrodes disposed along the distal end portion of the lead body,
a plurality of terminals disposed along the proximal end portion of the lead body, and
a plurality of conductors electrically coupling the plurality of electrodes to the plurality of terminals;

a control module electrically coupled to the plurality of electrodes, the control module comprising
a housing, and
an electronic subassembly disposed in the housing; and
the connector of claim 1 coupled to the housing of the control module;
wherein the proximal end portion of the lead body is configured and arranged for insertion into the port of the connector.

20. The connector of claim 1, wherein each of the pockets is defined, at least in part, by axial indentations in both of the first housing element and the second housing element.

* * * * *